(12) United States Patent
Fix et al.

(10) Patent No.: US 9,719,913 B2
(45) Date of Patent: Aug. 1, 2017

(54) OUTER PART FOR A DEVICE AND DEVICE

(71) Applicant: Robert Bosch GmbH, Stuttgart (DE)

(72) Inventors: Richard Fix, Gerlingen (DE); Andreas Krauss, Tuebingen (DE); Michael Badeja, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 290 days.

(21) Appl. No.: 14/314,902

(22) Filed: Jun. 25, 2014

(65) Prior Publication Data

US 2015/0000413 A1   Jan. 1, 2015

(30) Foreign Application Priority Data

Jun. 27, 2013 (DE) .......................... 10 2013 212 512

(51) Int. Cl.
  *G01N 21/01* (2006.01)
  *G01N 29/032* (2006.01)
  *G01N 29/036* (2006.01)

(52) U.S. Cl.
  CPC ........... *G01N 21/01* (2013.01); *G01N 29/032* (2013.01); *G01N 29/036* (2013.01); *G01N 2291/045* (2013.01); *G01N 2291/052* (2013.01)

(58) Field of Classification Search
  CPC ...... G01N 21/35; G01N 21/01; G01N 29/032; G01N 29/036; G01N 2291/045; G01N 2291/052
  See application file for complete search history.

(56) References Cited

U.S. PATENT DOCUMENTS

2009/0039267 A1* 2/2009 Arndt ................. G01N 21/3504
                                                250/353
2011/0248904 A1* 10/2011 Miyawaki ............ G02B 27/017
                                                345/7

FOREIGN PATENT DOCUMENTS

DE    10 2004 044145      4/2006

* cited by examiner

*Primary Examiner* — David Porta
*Assistant Examiner* — Mindy Vu
(74) *Attorney, Agent, or Firm* — Norton Rose Fulbright US LLP; Gerard Messina

(57) ABSTRACT

An outer part for a device which is attachable thereto as a housing and/or an attachment part, a first reflective surface and a second reflective surface being formed on the outer part so that at least one signal emitted by an optical and/or acoustic source is directly or indirectly deflectable onto at least one detector surface of an optical and/or acoustic detector, an optical path being configured as a cavern or continuous recess in the outer part or as a depression of a boundary surface of the outer part, the optical path having at least one opening via which at least one substance is transferable into the optical path, and the at least one signal being deflectable into the optical path to the second reflective surface which is formed at a second end of the optical path with the first reflective surface at a first end of the optical path.

19 Claims, 2 Drawing Sheets

OUTER PART FOR A DEVICE AND DEVICE

RELATED APPLICATION INFORMATION

The present application claims priority to and the benefit of German patent application no. 10 2013 212 512.7, which was filed in Germany on Jun. 27, 2013, the disclosure of which is incorporated herein by reference.

FIELD OF THE INVENTION

The present invention relates to an outer part for a device. The present invention further relates to a device.

BACKGROUND INFORMATION

German patent document DE 10 2004 044 145 B3 discusses a reflector module for a photometric gas sensor. The reflector module is configured as a cover for a bottom part on which an infrared radiation source and an infrared detector are mounted, a measuring gas being diffusible into the measuring volume covered by the reflector module. At least two reflective inner surfaces are formed on the reflector module in such a way that infrared radiation emitted by the infrared radiation source is deflectable along an absorption section onto the infrared detector. A concentration of the measuring gas is to be ascertainable with the aid of an analysis of the absorption of the infrared radiation along the absorption section.

SUMMARY OF THE INVENTION

The present invention creates an outer part for a device having the features described herein and a device having the features described herein.

The present invention allows a sensor for detecting, analyzing and/or measuring at least one substance to be integrated into a device, in particular into a mobile device, without increasing a volume and/or a space requirement of the device for this purpose. With an implementation of the present invention, in particular the formation of an additional measuring volume on the device, within which the at least one substance is detected/analyzed, is dispensed with. Instead, the conventionally required measuring volume may be integrated into an outer part of the device, without having to increase the dimensions of the outer part. A volume that conventionally goes unused on the device may thus be used for detecting/analyzing the at least one substance.

Due to the present invention, a measuring section for detecting the at least one substance to be detected and/or to be analyzed of at least several millimeters, in particular of several centimeters, may be implemented, without increasing a volume and/or a space requirement of the device having the integrated sensor for detecting/analyzing the at least one substance. In particular, a mobile device may thus be expanded by such a sensor, without (significantly) changing its appearance. Instead, due to a lightweight, sleek, manageable and/or comparatively small configuration of the device, its simple transportability/portability and its attractive configuration remain ensured. Also the number of materials usable for producing the device is (marginally) limited by the integration of the present invention.

In one advantageous specific embodiment, the outer part, which may be attached to the device as a housing part, is a cover glass and made entirely of at least one translucent material. The outer part may thus, for example, be configured as a cover glass of a smart phone, of a tablet, of a watch, of a mobile telephone, of a display, of a household appliance, of an entertainment device, of a warning device, of a measuring device, of an analysis device or of a medical technology device. The outer part may also be used as an eyeglass lens, in particular of electric eyeglasses. A volume that conventionally goes unused in many devices may thus be used for detecting/analyzing at least one substance.

In one further advantageous specific embodiment, the outer part, which is attachable to the device as an attachment part, may be an eyeglass frame, a frame temple or a wristband. The sensor for detecting and/or analyzing the at least one substance is also easy to integrate in this way.

The at least one optical and/or acoustic signal reflected off the first reflective surface may be deflectable with the aid of the second reflective surface in such a way that the at least one optical and/or acoustic signal is deflectable onto the at least one detector surface of the optical and/or acoustic detector with the aid of the second reflective surface after passing once through the optical path, or with the aid of the first reflective surface after passing twice through the optical path. Both specific embodiments are easy to implement.

In one further advantageous refinement, the optical path is filled at least partially with a porous and/or semipermeable material. The at least one opening may also be covered by at least one porous and/or semipermeable diaphragm. It is reliably ensurable in both cases that the at least one substance to be detected is diffused into the optical path, while a penetration of dirt particles into the at least one optical path is reliably prevented.

In another advantageous refinement, the optical path includes an optical and/or acoustic waveguide. The optical and/or acoustic waveguide may be at least partially covered with a sensitive contact layer. An optical property of the optical and/or acoustic waveguide may thus be changed due to a contact of the at least one substance with the sensitive contact layer. This also ensures reliable detectability and/or a precise and error-free concentration measurement of the at least one substance to be detected.

In addition, the optical path may be formed as a depression in an inner surface of the outer part and have at least one opening on the inner surface. Such a configuration of the outer part ensures good protection of the optical path from dirt.

In one further advantageous specific embodiment, the side walls of the optical path are coated with a reflective material. In combination with a suitable reflector, the measuring section is extended by the additional reflections.

The advantages described above are also ensured with a device having such an outer part.

The device may include an evaluation unit, which is configured to establish at least one piece of information regarding an occurrence, a frequency, a physical property and/or a chemical property of the at least one substance, taking into consideration at least one sensor signal provided by the optical and/or acoustic detector regarding an intensity and/or a spectral distribution of the at least one optical and/or acoustic signal impinging on the at least one detector surface of the optical and/or acoustic detector. The device is thus easy to equip with a sensor system which is suitable for detecting, analyzing and/or measuring the at least one substance.

Moreover, the evaluation unit may additionally be configured to establish a setpoint frequency distribution and/or a setpoint intensity of the at least one optical and/or acoustic signal emitted by the optical and/or acoustic source and to appropriately control the optical and/or acoustic source, taking into consideration the at least one established piece of information. A particularly advantageous and informative establishment of the setpoint frequency distribution will be addressed in greater detail below.

In one further advantageous specific embodiment, the evaluation unit is additionally configured to establish the at least one piece of information by additionally taking an output signal of a light barrier into consideration. For example, a sudden drop in the intensity of the at least one optical and/or acoustic signal impinging on the at least one detector surface may thus be reliably detected due to a foreign object which is present in the optical path. The at least one optical and/or acoustic signal (e.g., infrared radiation, acoustic signal) may also be used to detect a foreign body using modulation. If the signal does not arrive at all at the detector, this may be assessed as a blockage/clogging of the measuring section. An additional light barrier is thus not required.

In one refinement, this composition may additionally be used for particle measurement. By pivoting of the device, the particles may be supplied to an opening of the optical path. A detector perpendicular to the light path could thus also be used for particle measurement with the aid of scattered light.

The optical and/or acoustic source and the optical and/or acoustic detector may be situated on a shared circuit board of the device. The components cooperating with the outer part may thus also be accommodated in the device in a space-saving manner.

Further features and advantages of the present invention are described hereafter based on the figures.

DETAILED DESCRIPTION

Figure 1A:
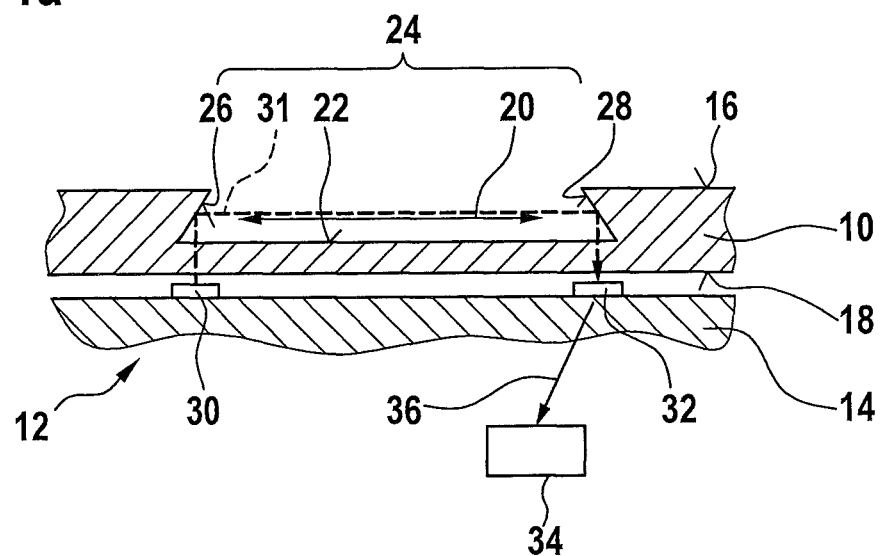
FIG. 1a shows a schematic cross section of a first specific embodiment of the outer part.
Figure 1B:
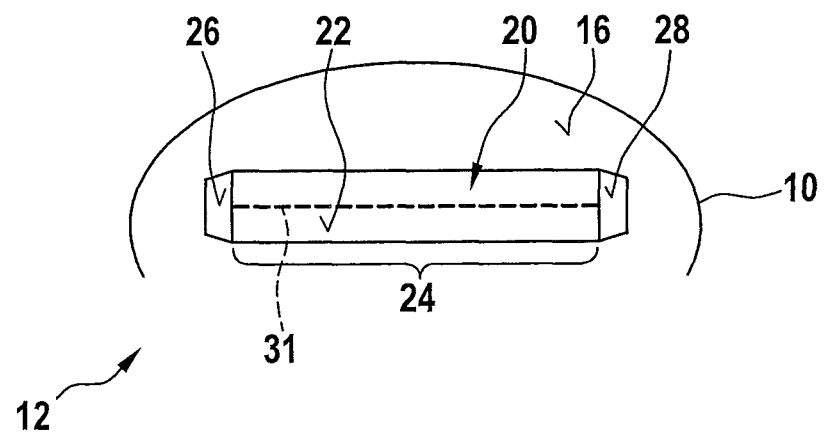
FIG. 1b shows a schematic top view onto a first specific embodiment of the outer part.

FIGS. 1a and 1b show a schematic cross section of and a schematic top view onto a first specific embodiment of the outer part.

Outer part 10 shown schematically in FIG. 1a and FIG. 1b is situatable on a (partially shown) device 12. Outer part 10 may be used as a housing part of a housing of device 12 and/or as an attachment part for attaching device 12 to a body and/or to an object. Outer part 10 is configured in such a way that it is attachable to at least one further component 14 of device 12, such as a circuit board 14 (a printed circuit board, a chip). Outer part 10 may in particular be attachable to the at least one further component 14 of device 12 with the aid of a screw, clip and/or adhesive joint. It is pointed out that the configuration options of outer part 10 are not limited to one particular attachment type of outer part 10 to the at least one further component 14 of device 12.

FIGS. 1a and 1b show outer part 10 in a web- or disk-shaped manner. After its attachment to the at least one further component 14, outer part 10 has a boundary surface which may be described as an outer surface 16 and which is directed away from the at least one further component 14. Another boundary surface of the outer part, which is directed to the at least one further component 14, may be described as an inner surface 18. However, it is pointed out that the configuration of outer part 10 shown in FIGS. 1a and 1b should merely be interpreted by way of example. For example, outer part 10 may also be configured to be band-shaped or helical.

Outer part 10 has an optical path 20, which is configured as a depression in a boundary surface of outer part 10, e.g., in outer surface 16. For example, optical path 20 configured as a depression has a bottom surface 22, which is situated in a volume delimited on a first side by a first plane including outer surface 16 and on an (opposing) second side by a second plane including inner surface 18. Bottom surface 22 may in particular be parallel to at least one of surfaces 16 and 18.

Optical path 20 has at least one opening 24, via which at least one substance (to be ascertained and/or to be analyzed) is transferable into optical path 20. In the specific embodiment of FIGS. 1a and 1b, the at least one opening 24 is situated on outer surface 16. As an alternative, however, optical path 20 may also be configured as a depression in inner surface 18. In this case, optical path 20 has an opening 24 which is formed on inner surface 18.

As an alternative to configuring optical path 20 as a depression, outer part 10 may also have an optical path 20 configured as a cavern. In addition to bottom surface 22, in this case a top surface directed away from the bottom surface is formed for optical path 20, bottom surface 22 and top surface 24 being perforated at most by the at least one opening 24. Bottom surface 22 and the top surface may in particular be made of a gas-impermeable material. In this case as well, the position of optical path 20 in outer part 10 is generally describable in such a way that optical path 20 is located in a volume delimited by planes having surfaces 16 and 18.

Outer part 10 may also have an optical path 20 which is configured as a continuous recess (from outer surface 16 to inner surface 18). A bottom surface 22 may be implemented by at least one further component 14 in this case.

If optical path 20 is configured as a depression in outer surface 16 of outer part 10, as a continuous recess or as a cavern having an opening 24 to outer surface 16, simple cleaning of the same is possible. In contrast, soiling of optical path 20 is easily preventable by configuring optical path 20 as a depression in inner surface 18 and/or with the at least one opening 24 only on inner surface 18.

Optical path 20 configured as a depression, as a continuous recess or as a cavern is configured with a first reflective surface 26 at a first end and with a second reflective surface 28 at a second end. At least one optical and/or acoustic signal 31 emitted by an optical and/or acoustic source 30 of device 12 (having attached outer part 10) is deflectable into optical path 20 to second reflective surface 28 with the aid of first reflective surface 26. With the aid of second reflective surface 28, the at least one optical and/or acoustic signal 31 reflected off first reflective surface 26 is deflectable in such a way that optical and/or acoustic signal 31 is directly or indirectly deflectable onto at least one detector surface (not illustrated) of an optical and/or acoustic detector 32 of device 12 (having attached outer part 10). In the specific embodiment of FIGS. 1a and 1b, optical and/or acoustic signal 31 is deflectable onto the at least one detector surface of optical and/or acoustic detector 32 with the aid of second reflective surface 28 already after passing once through optical path 20. Optionally, at least one further reflective component is also usable for deflecting the at least one optical and/or acoustic signal 31 reflected off second reflective surface 28 to optical and/or acoustic detector 32. A particularly advantageous refinement in this regard will be addressed below.

With the aid of the advantageous configuration of optical path 20, a measuring section for detecting/analyzing the at least one substance based on its absorption and/or emission is thus implemented in the form of a cavity, a continuous recess or a depression in a component which previously generally went unused. Since housing parts and/or attachment parts on a device 12 are often configured to be comparatively large, a sufficient length of the measuring section is easy to implement, without increasing a volume and/or a space requirement of device 12 for this purpose. Due to the easily implementable sufficient length of the measuring section, the at least one substance may be reliably detected/analyzed, precise measuring results and low error frequency being ensured. Outer part 10 thus advantageously contributes to the integration of a sensor for detecting/analyzing the at least one substance into a device 12, in particular into a mobile device 12.

For example, outer part 10, which is attachable to device 12 as a housing part, may be a cover glass and made (entirely) of at least one translucent material. Since a cover glass is generally configured to be comparatively large, in this case a sufficiently long optical path 20 for reliable detection/analysis of the at least one substance is easily possible, in addition to a user-friendly configuration. Outer part 10 may in particular be a cover glass of a smart phone, of a tablet, of a watch (e.g., a wrist watch), of a mobile telephone, of a display, of an entertainment device, of a household appliance, of a warning device, of a measuring device, of an analysis device or of a medical technology device. Cover glass 10 may also be an eyeglass lens, in particular of electric eyeglasses.

However, outer part 10 may also be made of an opaque material. For example, outer part 10 may also be a cover, such as a battery cover.

An outer part 10 which is attachable to device 12 as an attachment part may, e.g., be an eyeglass frame, a frame temple or a wristband. Device 12 may be configured as a mobile device. For example, device 12 may be a smart phone, a tablet, a watch (specifically a wrist watch), eyeglasses (which may have integrated electronics), a mobile telephone, a display, an entertainment device (e.g., a television or an electric game), a household appliance, a warning device (such as a fire alarm or a gas alarm), a measuring device, an analysis device (specifically a fuel analysis device), or a medical technology device (such as an analysis device for analyzing a body fluid, a breathing gas analysis device or a lab-on-chip analysis device). However, the configuration options of device 12 are not limited to the examples listed here.

The body of outer part 10, which at least partially surrounds optical path 20 formed therein, may be made of at least one rigid material. However, as an alternative, the body of outer part 10 may also be configured to be elastic, such as an elastic band. In both cases, optical path 20 may already be formed in outer part 10 during an injection molding process which is carried out to produce the outer part.

Optical path 20 may extend along a center longitudinal axis running parallel to at least one of surfaces 16 and 18. In the specific embodiment of FIGS. 1a and 1b, first reflective surface 26 and second reflective surface 28 are each oriented at an angle of inclination between 10° and 80°, in particular between 25° and 65°, which may be between 35° and 55°, relative to the center longitudinal axis. Specifically, first reflective surface 26 and second reflective surface 28 may each be oriented at an angle of inclination of 45° relative to the center longitudinal axis. Another advantageous configuration of first reflective surface 26 and second reflective surface 28 will be addressed below.

One further advantageous specific embodiment provides for a reflector having two angles of inclination which are orthogonal to each other. The resulting reflection surface may in particular be rounded, so that a reflection at the reflective side walls of measuring section 20 is ensured, and the effective measuring section is thereby lengthened.

Device 12 may additionally include an evaluation unit 34, which is configured to establish at least one piece of information regarding an occurrence of the at least one substance, a frequency (concentration) of the at least one substance, a physical property of the at least one substance and/or a chemical property of the at least one substance, taking into consideration at least one sensor signal 36 provided by optical and/or acoustic detector 32 regarding an intensity and/or a spectral distribution of the at least one optical and/or acoustic signal 31 impinging on the at least one detector surface of optical and/or acoustic detector 32. With the aid of an interaction of the at least one substance with the at least one acoustic and/or optical signal 31, the at least one substance may be reliably detected and/or analyzed for its frequency, at least one of its physical properties and/or at least one of its chemical properties. Optionally, at least one provided comparison signal regarding an intensity and/or a spectral distribution of the at least one optical and/or acoustic signal 31 emitted by optical and/or acoustic source 30 may also be taken into consideration when the at least one piece of information is established.

For example, the at least one substance to be detected/analyzed may be at least one gas, in particular carbon dioxide, carbon monoxide, ozone and/or a combustible gas, at least one liquid, e.g., a fuel, and/or at least one substance dissolved in a liquid, specifically in a body fluid. The at least one substance may be gaseous, liquid, solid and/or particulate. The at least one substance may be understood to mean, for example, at least one molecule/macromolecule to be detected specifically in optical path 20. The at least one substance may also be understood to mean the medium present in the interior of optical path 20.

The at least one substance may diffuse or seep into optical path 20, for example. The diffusion of the at least one substance into optical path 20 may take place in particular from surroundings of outer part 10 (without additional actuation). However, the at least one opening 24 may also be configured in such a way that the at least one substance is easily introducible into optical path 20 by a person.

A specificity of the detection/verification of the at least one substance may be increased in that optical path 20 is filled at least partially with a porous and/or semipermeable material and/or in that the at least one opening 24 is covered with at least one porous and/or semipermeable diaphragm. In this way it may be specifically ensured that only the at least one substance to be detected reaches optical path 20, while a penetration of a foreign object (e.g., moisture) into optical path 20 is suppressible. Moreover, a soiling of optical path 20 is thus preventable. The at least one porous and/or semipermeable material filled into optical path 20 may in particular have a particular affinity for the at least one substance to be detected. Moreover, optical path 20 may also have a (partial) coating, which has a particular affinity for the at least one substance.

An impairment of a detection or of a measurement due to a foreign object located in or on optical path 20 may additionally be prevented by configuring evaluation unit 34 to establish at least one piece of information by additionally taking an output signal of a light barrier into consideration.

For example, it may thus be recognized that a lower intensity of the at least one optical and/or acoustic signal 31 impinging on optical and/or acoustic detector 32 occurs only as a result of the penetration of a foreign object, such as a fingertip and/or a cleaning cloth, into the optical path.

In one advantageous specific embodiment, evaluation unit 34 may additionally be configured to establish a setpoint frequency distribution and/or a setpoint intensity of the at least one optical and/or acoustic signal 31 emitted by optical and/or acoustic source 30 and to appropriately control optical and/or acoustic source 30, taking into consideration the at least one established piece of information. For example, an intensity of the at least one optical and/or acoustic signal 31 may be increased in a targeted manner after the at least one substance has been detected. In this way, energy which is required for measuring a concentration of the at least one substance may be saved if this substance is not present. Moreover, the frequency distribution of the at least one optical and/or acoustic signal 31 may be variable in a targeted manner.

In one further advantageous specific embodiment, a visible light may be emitted as the at least one optical and/or acoustic signal 31 by the actuated optical and/or acoustic source 30, the color of the light being used as an indicator of at least one detected substance and/or of a concentration of the at least one detected substance. For example, good ambient air which is established may be indicated with the aid of a green light, while red light is emitted with the aid of the actuated source 30 after poor ambient air was established.

Optical and/or acoustic source 30 and optical and/or acoustic detector 32 may be situated in a shared circuit board 14, in particular integrated jointly into a chip/housing, of device 12. It is thus not necessary to situate optical and/or acoustic source 30 and optical and/or acoustic detector 32 directly on outer part 10. Furthermore, optical and/or acoustic source 30 and/or the optical and/or acoustic detector may in each case also include multiple components which may be situated separately from each other. Since the measuring section for detecting the at least one substance is not located on/within circuit board 14, great configuration freedom in configuring circuit board 14 (printed circuit board) is ensured. An adjustment complexity for situating components 30 and 32 in a position with respect to each other is also dispensed with in this case.

Evaluation unit 34 may in particular be integrated into an electronic system of device 12. Device 12 may thus be configured with the advantageous functionality for analyzing, detecting and/or measuring the at least one substance, without having to situate an additional electrical component on device 12.

Figure 2:
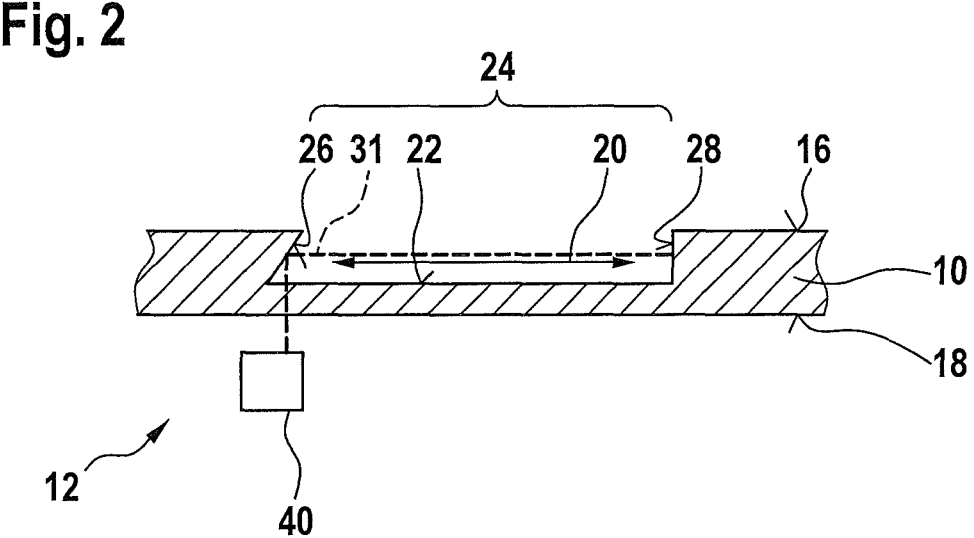
FIG. 2 shows a schematic cross section of a second specific embodiment of the outer part.

FIG. 2 shows a schematic cross section of a second specific embodiment of the outer part.

In the specific embodiment of FIG. 2, the optical and/or acoustic source and the optical and/or acoustic detector are integrated into a single component 40. With the aid of second reflective surface 28, the at least one optical and/or acoustic signal 31 reflected off first reflective surface 26 is deflectable in such a way that optical and/or acoustic signal 31 is deflectable onto the at least one detector surface of component 40 with the aid of first reflective surface 26 after passing twice through optical path 20. The measuring section for detecting, measuring and/or analyzing the at least one substance to be detected and/or to be measured is thus doubled without lengthening optical path 20. The specific embodiment shown in FIG. 2 is therefore particularly well-suited for an integration into a comparatively small outer part 10.

On such an outer part 10, second reflective surface 28 may be inclined by 90° relative to bottom surface 22/the center longitudinal axis. For example, first reflective surface 26 may be oriented to be inclined by 45° relative to bottom surface 22/the center longitudinal axis. Otherwise, reference is made to the comments above with respect to the configuration of outer part 10 and device 12.

In one advantageous refinement, reflective surfaces 26 and 28 may also be configured to be adjustable/extendible. For example, a reflective coating may be applied to a piezoresistive layer for this purpose.

In one further advantageous specific embodiment, optical path 20 may also include an optical and/or acoustic waveguide, the optical and/or acoustic waveguide being at least partially covered by a sensitive contact layer. The sensitive contact layer may be a gas-sensitive layer, for example. In addition, it is also possible to detect at least one poorly absorbing substance if the sensitive contact layer specifically binds the same.

What is claimed is:

1. An outer part for a device which is attachable to at least one further component of the device at least one of as a housing part and as an attachment part, the outer part comprising:
    an outer part arrangement, wherein a first reflective surface and a second reflective surface are formed on the outer part so that at least one signal emitted by a source of the device having the attached outer part is deflectable onto the second reflective surface with the aid of the first reflective surface, and the at least one signal reflected off the first reflective surface is deflectable with the aid of the second reflective surface so that the at least one signal is directly or indirectly deflectable onto at least one detector surface of a detector of the device having the attached outer part,
    wherein a path is configured as a continuous recess in an outer surface of the outer part arrangement, or as a depression in the outer surface of the outer part arrangement, and the path is configured to allow for at least one substance to be transferred into the path, the first reflective surface being formed at a first end of the path so that the at least one signal emitted by the source is deflectable through the path to the second reflective surface formed at a second end of the path with the aid of the first reflective surface.

2. The outer part of claim 1, wherein the at least one signal is at least one optical signal, the source is an optical source, the detector is an optical detector, and the path is an optical path.

3. The outer part of claim 2, wherein the outer part, which is attachable to the device as a housing part, is a cover glass and made entirely of at least one translucent material.

4. The outer part of claim 3, wherein the device is a portable electronic device.

5. The outer part of claim 2, wherein the outer part, which is attachable to the device as an attachment part, is an eyeglass frame, a frame temple or a wristband.

6. The outer part of claim 2, wherein the at least one optical signal reflected off the first reflective surface is deflectable with the aid of the second reflective surface so that the at least one optical signal is deflectable onto the at least one detector surface of the optical detector with the aid of the second reflective surface after passing once through the optical path, or with the aid of the first reflective surface after passing twice through the optical path.

7. The outer part of claim 2, wherein the optical path is filled at least partially with at least one of a porous material and a semipermeable material.

8. The outer part of claim 2, wherein the at least one opening is covered by at least one diaphragm that is at least one of porous and semipermeable.

9. The outer part of claim 2, wherein the optical path includes an optical waveguide, which is at least partially covered by a sensitive contact layer.

10. The outer part of claim 1, wherein the outer part is an eyeglass lens.

11. The outer part of claim 1, wherein the device is a pair of eyeglasses.

12. The outer part of claim 1, wherein a first and a second wall of the path are coated with a reflective surface.

13. A device, comprising:
a device arrangement; and
an outer part for the device arrangement which is attachable to at least one further component of the device arrangement at least one of as a housing part and as an attachment part, the outer part including an outer part arrangement, wherein:
a first reflective surface and a second reflective surface is formed on the outer part so that at least one signal emitted by a source of the device arrangement having the attached outer part is deflectable onto the second reflective surface with the aid of the first reflective surface, and the at least one signal reflected off the first reflective surface is deflectable with the aid of the second reflective surface so that the at least one signal is directly or indirectly deflectable onto at least one detector surface of a detector of the device arrangement having the attached outer part; and
a path is configured as a continuous recess in an outer surface of the outer part arrangement, or as a depression in the outer surface of the outer part arrangement, and the path is configured to allow for at least one substance to be transferred into the path, the first reflective surface being formed at a first end of the path so that the at least one signal emitted by the source is deflectable through the path to the second reflective surface formed at a second end of the path with the aid of the first reflective surface.

14. The device of claim 13, wherein the at least one signal is at least one optical signal, the source is an optical source, the detector is an optical detector, and the path is an optical path.

15. The device of claim 14, further comprising:
an evaluation unit to establish at least one piece of information regarding at least one of an occurrence, a frequency, a physical property and a chemical property of the at least one substance, taking into consideration at least one sensor signal provided by the optical detector regarding at least one of an intensity and a spectral distribution of the at least one optical signal impinging on at least one detector surface of the optical detector.

16. The device of claim 15, wherein the evaluation unit is further configured to establish at least one of a setpoint frequency distribution and a setpoint intensity of the at least one optical signal emitted by the optical source and to appropriately control the optical source, taking into consideration the at least one established piece of information.

17. The device of claim 15, wherein the evaluation unit is further configured to establish the at least one piece of information by additionally taking an output signal of a light barrier into consideration.

18. The device of claim 14, wherein the optical source and the optical detector are situated on a shared circuit board of the device.

19. A device, comprising:
a device arrangement;
an outer part for the device arrangement which is attachable to at least one further component of the device arrangement at least one of as a housing part and as an attachment part, the outer part including an outer part arrangement, wherein:
a first reflective surface and a second reflective surface are formed on the outer part so that at least one optical signal emitted by an optical source of the device arrangement having the attached outer part is deflectable onto the second reflective surface with the aid of the first reflective surface, and the at least one optical signal reflected off the first reflective surface is deflectable with the aid of the second reflective surface so that the at least one optical signal is directly or indirectly deflectable onto at least one detector surface of an optical detector of the device arrangement having the attached outer part, and
an optical path is configured as a continuous recess in an outer surface of the outer part arrangement, or as a depression in the outer surface of the outer part arrangement, and the optical path is configured to allow for at least one substance to be transferred into the optical path, the first reflective surface being formed at a first end of the optical path so that the at least one optical signal emitted by the optical source is deflectable through the optical path to the second reflective surface formed at a second end of the optical path with the aid of the first reflective surface; and
an evaluation unit to establish at least one piece of information regarding at least one of an occurrence, a frequency, a physical property and a chemical property of the at least one substance, taking into consideration at least one sensor signal provided by the optical detector regarding at least one of an intensity and a spectral distribution of the at least one optical signal impinging on at least one detector surface of the optical detector,
wherein the evaluation unit is further configured to establish at least one of a setpoint frequency distribution and a setpoint intensity of the at least one optical signal emitted by the optical source and to appropriately control the optical source, taking into consideration the at least one established piece of information.

* * * * *